United States Patent [19]

Kolter et al.

[11] Patent Number: 6,046,277
[45] Date of Patent: Apr. 4, 2000

[54] USE OF REDISPERSIBLE POLYMER POWDERS OF POLYMER GRANULES FOR COATING PHARMACEUTICAL OR AGROCHEMICAL USE FORMS

[75] Inventors: Karl Kolter, Limburgerhof; Kristin Tiefensee, Westheim; Reinhold Stadler, Kirrweiler; Katrin Zeitz, Ludwigshafen, all of Germany

[73] Assignee: BASF Aktiengesellschaft, Ludwigshafen, Germany

[21] Appl. No.: 09/037,791

[22] Filed: Mar. 10, 1998

[30] Foreign Application Priority Data

Mar. 10, 1997 [DE] Germany ............... 197 09 532

[51] Int. Cl.[7] .............. C08L 35/00; C08L 39/04
[52] U.S. Cl. .......... 525/205; 525/203; 524/417; 524/451; 524/316; 524/322
[58] Field of Search .................. 525/203, 205; 524/447, 417, 35, 492, 493, 494, 451, 316, 322

[56] References Cited

U.S. PATENT DOCUMENTS 5,252,704  10/1993  Bright ....................... 528/501
5,490,999  2/1996  Villagran et al. .................. 426/633
5,681,892  10/1997  Weidner et al. .................. 525/58

FOREIGN PATENT DOCUMENTS 42 20 782  1/1994  European Pat. Off. .

OTHER PUBLICATIONS

Cellulosen Chem. Ed. 13, 58–64, 71–74, 1932.

Primary Examiner—James J. Seidleck
Assistant Examiner—U. K. Rajguru
Attorney, Agent, or Firm—Keil & Weinkauf

[57] ABSTRACT

The use of redispersible polymer powders or polymer granules for coating pharmaceutical or agrochemical use forms, consisting of a) 10–95% by weight of polyvinyl acetate,
b) 5–90% by weight of an N-vinylpyrrolidone-containing polymer,
c) 0–20% by weight of another water-soluble or water-swellable substance and
d) 0–20% by weight of a water-insoluble dusting agent with or without
e) other additives.

8 Claims, No Drawings

USE OF REDISPERSIBLE POLYMER POWDERS OF POLYMER GRANULES FOR COATING PHARMACEUTICAL OR AGROCHEMICAL USE FORMS

The present invention relates to the use of redispersible polymer powders or polymer granules consisting of polyvinyl acetate and N-vinylpyrrolidone-containing polymers for coating pharmaceutical or agrochemical use forms, it being possible to control accurately the release of the active ingredient from the use form.

Solid pharmaceutical use forms such as tablets, capsules, pellets, granules, crystals etc. are coated, ie. provided with a film coating, for a wide variety of reasons. Thus, for example, an unpleasant odor or taste can be masked, and swallowability can be improved. The stability of the active ingredient can be increased by the coating through less water vapor and oxygen entering the interior of the tablet. The use forms have a better appearance and can be distinguished better by incorporating dyes. It is furthermore possible in particular to adjust the rate of release of the active ingredient by the film coating. These criteria also apply to agrochemical use forms in a similar way.

A general distinction is made between instant release forms and delayed or slow release forms.

The intention with instant release forms is that the active ingredient is released in the shortest time possible. In this case, the coating must impede only slightly, if at all, the release of the active ingredient from the core. In pharmaceutical technology, instant release forms are preparations from which more than 80% of the active ingredient are released within one hour.

By contrast, the delay of release from delayed release forms is, for example, in order to prevent plasma level peaks and thus possible side effects, or to reduce the frequency of intake. In the case of coated delayed release forms, a film coating slows down release of the medicinal substance. Frequently employed for this purpose are water-insoluble cellulose derivatives such as ethylcellulose or (meth) acrylate copolymers, in particular Eudragit® NE, RS or RL (Röhm Pharma, Weiterstadt). For Eudragit® RS and RL it is recommended to add from 10 to 20% by weight of plasticizer, based on the film former. In the case of ethylcellulose, an even higher plasticizer content (about 30% by weight) is indispensible. Only Eudragit® NE requires no plasticizer because it has a very low glass transition temperature and minimum film formation temperature. However, this makes it tacky and difficult to process.

U.S. Pat. No. 5,252,704 describes the production of redispersible polymer powders using polyvinylpyrrolidone as dispersing auxiliary. The stated area of use is in the manufacture of cement. Pharmaceutical applications are, by contrast, not mentioned.

DE-B-4341156 describes the use of water-dispersible polymer dispersion powders with a core/shell structure as drug carriers, wherein the pharmaceutical processing merely comprises the dry polymer powder being mixed in with the medicinal substance, followed by compression. Matrix forms of this type differ fundamentally from coated delayed release forms.

DE-A-4220782 describes processes for producing solid pharmaceutical delayed release forms by application of a binder to a core containing active ingredients. The binders used in this case are (meth)acrylate-based polymers.

It is an object of the present invention to find polymer powders or polymer granules consisting of a water-insoluble and water-soluble polymer which are completely redispersible and suitable for uniform coating of pharmaceutical and agrochemical use forms. It was intended that the forms produced in this way permit easily controllable release of the active ingredients.

We have found that this object is achieved by the use of redispersible polymer powders or polymer granules consisting of a) 10–95% by weight of polyvinyl acetate, b) 5–90% by weight of an N-vinylpyrrolidone-containing polymer, c) 0–20% by weight of another water-soluble or water-swellable substance and d) 0–20% by weight of a water-insoluble dusting agent with or without e) other additives, for coating pharmaceutical or agrochemical use forms.

It is possible with the aid of these polymers to control accurately the release of the active ingredient from the use form, so that both instant release and delayed or slow release forms can be made available.

The redispersible polymer powders are produced by initial emulsion polymerization of vinyl acetate, then addition of the N-vinylpyrrolidone-containing polymer, with or without other auxiliaries, to the resulting shear-stable and fine-particle dispersion, and spray-drying of the mixture. Examples of preferred N-vinylpyrrolidone-containing polymers are polyvinylpyrrolidone and vinyl acetate/ vinylpyrrolidone copolymers.

The K values of the polymers should be in the range from 10 to 350, preferably 30 to 150, particularly preferably in the range from 50 to 90. The K value required in each case can be adjusted in a conventional way by the choice of the polymerization conditions, for example the polymerization time and the initiator concentration. The K values are measured by the method of Fikentscher, Cellulosechemie, 13 (1932) 58–64 and 71–74, at 25° C. in 0.1% by weight aqueous solution.

Addition of fine-particle, water-insoluble spraying aids during the spray drying is able to prevent adhesion of the particles formed. It is particularly advantageous in this connection for these spraying aids to be atomized into the spray dryer. However, it is also possible to add the spraying aids to the dispersion to be sprayed, or to mix them in only after the spray-drying to prevent the particles caking together. Dusting agents which can be used are up to 20% by weight, based on the solids content, of fine-particle water-insoluble substances, in particular at least one representative from the group of cellulose, preferably microcrystalline cellulose, disperse silica, talc, bentonite, magnesium stearate or a calcium phosphate.

The emulsion polymerization is carried out in a conventional way at from 50° C. to 95° C., preferably from 60° C. to 80° C., in the presence of known polymerization initiators.

Suitable and preferred polymerization initiators are free-radical formers, for example peroxides such as, preferably peroxosulfates, peroxodisulfates and azo compounds such as azodiisobutyronitrile.

Emulsifiers which can be employed are both ionic and nonionic emulsifiers or mixtures thereof. Their total concentration is from 0.2 to 10% by weight, preferably from 0.4 to 7% by weight, based on the total monomer content. It is furthermore possible to employ as other auxiliaries up to 20% by weight, based on the solids content, of water-soluble or water-swellable protective colloids such as cellulose derivatives, preferably hydroxypropylmethylcellulose, methylcellulose or hydroxyethylcellulose, galactomannan, pectin, xanthan, polyvinyl alcohol, acrylate/methacrylate copolymers, sodium carboxymethyl-starch, cellulose, degraded starches, maltodextrins etc. The emulsifying auxiliaries can moreover be added before, during and after the polymerization.

The dispersion has a solids content of from 10 to 45% by weight, preferably from 15 to 35% by weight.

The sedimentation-stable polymer dispersion has average particle sizes of from 0.1 to 7 $\mu$m, preferably from 0.3 to 4 $\mu$m. The determination takes place in a conventional way, eg. by means of an ultracentrifuge, photon correlation spectroscopy or by determining the transmission of light. The particle size is normally controlled by the emulsifier concentration or the temperature.

The shear stability of the polyvinyl acetate dispersion is of crucial importance. Only very shear-stable dispersions are able to form adequately redispersible powders after spraying.

The shear stability is tested by shearing the dispersion using a knopped stirrer at 2000 rpm for 15 min and gravimetric determination of the coagulate after screening through a 125 $\mu$m screen. Shear-stable dispersions have coagulate contents of <0.1%.

The polyvinylpyrrolidone is preferably added as 10 to 50% by weight solution with continuous stirring. Coagulation may occur if added as solid or as more concentrated solution.

The spray drying takes place in a conventional way in spray towers with the dispersion which is to be dried being atomized by nozzles or disks. The hot gas, eg. air or nitrogen, can be fed in cocurrently or countercurrently, with the cocurrent process being particularly preferred because it leads to less temperature stress.

It is also possible to employ FSD (fluidized spray drying) technology, in which initial spray-drying is immediately followed by agglomeration in a fluidized bed. Freeze-drying is an alternative possibility.

The ratio by weight of polyvinyl acetate to polyvinylpyrrolidone and/or at least one copolymer of vinyl acetate and vinylpyrrolidone can be varied in the range from 95:5 to 10:90, whereby the release properties can be modified. The rate of release increases as the content of hydrophilic polyvinylpyrrolidone increases. It is possible in this way to adjust the release of pharmaceutical active ingredients from very slow (24 h) to very fast (0.25 h). Thus, instant release coatings are also possible, for which suitable and preferred combinations are those with a ratio by weight of polyvinyl acetate to polyvinylpyrrolidone and/or at least one copolymer of vinyl acetate and vinylpyrrolidone of <70:30. Release can furthermore be adjusted by adding other hydrophilic or lipophilic auxiliaries. The addition of hydrophilic auxiliaries, eg. hydroxypropylmethylcellulose, hydroxypropylcellulose, methylcellulose, hydroxyethylcellulose, galactomannan, pectin, xanthan, polyvinyl alcohol, acrylate/methacrylate copolymers, sodium carboxymethyl starch, or cellulose, degraded starches, maltodextrins etc. or else low molecular weight substances such as monosaccharides, disaccharides, sugar alcohols, inorganic water-soluble salts, amino acids, water-soluble acids, or their salts or surfactants, increases the rate of release and may additionally stabilize the dispersion.

Additional hydrophilic properties of the redispersible polymer powders according to the invention can be adjusted by using partially hydrolyzed polyvinyl acetate, in which case polyvinyl acetates with a degree of hydrolysis of up to 50 mol % are particularly used.

It is thus possible for instant release purposes in particular also to mix a combination of polyvinyl acetate with polyvinylpyrrolidone and/or at least one copolymer of vinyl acetate and vinylpyrrolidone in a ratio by weight of >70:30 with, for example, hydroxypropylmethylcellulose. In this case it is possible to add the hydroxypropylmethylcellulose during production of the redispersible polymer or else only during production of the coating dispersion. It is particularly preferred to use polyvinyl alcohol and/or hydroxypropylmethylcellulose.

Application of a delayed release coating can take place using a solution of the polymer in an organic solvent or, preferably, a 2–50% by weight, in particular a 10–30% by weight, dispersion of the polymer in water. The aqueous procedure has great advantages for technical reasons. However, fine-particle dispersions are thermodynamically unstable preparations which are very sensitive to stress factors such as temperature fluctuations, freezing, shearing, water evaporation, shaking etc. and thus become unusable. Surprisingly, it is possible to eliminate these disadvantages by using a redispersible product consisting of polyvinyl acetate and polyvinylpyrrolidone or vinyl acetate/vinylpyrrolidone copolymers, and other formulation aids.

The dispersion for coating pharmaceuticals or agrochemical use forms is preferably produced by introducing the redispersible powder consisting of polyvinyl acetate and polyvinylpyrrolidone and/or at least one copolymer of vinyl acetate and vinylpyrrolidone, preferably with hydrophilic or lipophilic additives into water with stirring. It is then possible to admix other auxiliaries customary for pharmaceutical coating purposes such as water-soluble or water-insoluble dyes (colored pigments), white pigments (eg. $TiO_2$), antistick agents (eg. talc, glycerol monostearate, magnesium stearate), suspension stabilizers, emulsifiers, thickeners, plasticizers etc. It is advantageous to suspend these solids in water before incorporation into the dispersion and to homogenize using a high-speed stirrer (Ultra-turrax) or a mill (corundum disk mill). This coating suspension is then sprayed onto pharmaceutical use forms by means of suitable equipment, eg. horizontal drum coaters, coating pans, fluidized bed equipment, resulting in a uniform homogeneous film which, after drying, requires no further heat treatment or curing. Films with a high content of polyvinyl acetate remain intact during release tests and thus slow down the transport of the active ingredient into the release medium; films with a low content of polyvinyl acetate disintegrate or disperse, and the medicinal substance is rapidly released.

The coated use forms are preferably solid preparations. By this are meant, inter alia, tablets, microtablets, coated tablets, pastilles, capsules, crystals, granules or pellets.

The release times required for agrochemicals, eg. crop protection agents, are distinctly higher than for pharmaceuticals. Release times of from 6 weeks to 6 months are required, depending on the season, plant variety and soil characteristics. These long delays in release can be adjusted by varying the thickness of the layer of the coating agent according to the invention applied to the active ingredient, and by additional chemical crosslinking.

Suitable crop protection agents are substances with herbicidal, growth-regulating, insecticidal and, in particular, fungicidal activity.

Preferred solid use forms for crop protection are granules and pellets.

Fungal pests are controlled with the fungicidal compositions expediently by allowing a fungicidally effective amount of the fungicidal composition to act, in or on the soil, on the seeds which have been sown or on the plants or seedlings developing therefrom.

The delayed release of the active ingredients means that it is possible to control the rate of release of the active ingredients in the soil in such a way that, for example in the case of the fungicidal crop protection agents, effective protection from fungal diseases can be maintained throughout the vegetation period. Uptake of active ingredient takes place continuously through the roots at the rate of the controlled release of the active ingredients formulated according to the invention, and the active ingredients are then distributed through the roots systemically in the plants.

Compared with the spray application of crop protection agents which is widely used to control fungi, the process according to the invention has the following advantages:

- A single application of the active ingredients formulated according to the invention to the soil, which advantageously takes place at the same time as sowing or planting of seedlings, is able to achieve effective protection of the plant against, for example, fungal diseases throughout the vegetation period.
- This makes the previously customary multiple spray application to the growing crop unnecessary, allowing considerable savings in effort.
- Application of the crop protection agents in the form of the formulation according to the invention means that smaller amounts of active ingredients have to be applied.
- Seed dressing can be omitted if the process according to the invention is used.

It is an essential feature of the present invention that the crop protection agents are present in a formulation with delayed release of active ingredient. Such controlled release of active ingredient makes it possible to maintain effective protection of the crop plants against fungal attack throughout the vegetation period with one application of the fungicidal composition according to the invention in the soil.

The granules are produced as coated granules by initially applying the active ingredients to solid granular carriers. The resulting granules containing active ingredient are then coated with suitable coating substances which result in delayed controlled release of active ingredients.

Examples of suitable solid carriers for the coated granules are mineral earths such as silica gel, silicas, silicates, talc, kaolin, limestone, lime, chalk, bole, loess, clay, dolomite, diatomaceous earth, calcium and magnesium sulfates, magnesium oxide, ground plastics, fertilizers such as ammonium sulfate, ammonium phosphate, ammonium nitrate, ureas, eg. crotonylidenediurea, isobutylidenediurea, and vegetable products such as cereal flour, cornflour, bark meal, wood meal and nutshell meal, cornmeal, cellulose powder. Fertilizers are advantageously used as carriers. Fertilizer granules or pellets are preferred as carrier, especially those containing phosphate.

The granules generally have a particle size range from 0.1 to 10 mm, preferably 0.5 to 8 mm, in particular 1 to 6 mm.

The active ingredients are generally applied to the carriers by spraying them on in the form of oil-in-water emulsions, emulsion concentrates, suspoemulsions, suspension concentrates or dissolved in organic solvents or, preferably, in water.

They are sprayed on, for example, in fluidized bed equipment or in drums or rotary disks in which the carrier granules are rolled, in perforated vessels with controlled guidance of the drying medium, expediently air, or in an air suspension process. The spraying on and the drying are generally carried out at from 10° C. to 110° C.

The carrier containing the applied active ingredient is subsequently enveloped with the polymer mixtures according to the invention.

The fungicidal compositions obtained in this way and provided with the enveloping layer can be used as such for the control according to the invention of fungi with controlled release of active ingredient.

However, it may also be advantageous additionally to apply active ingredient to these compositions from outside. The compositions obtained in this way permit further gradation of the controlled release of active ingredient, with the active ingredients applied to the outside of the enveloping layer being important for a more targeted initial action. It may additionally be advantageous also to use a second enveloping layer, which provides another possibility for controlling the delayed release of the active ingredients.

Besides the enveloping technique described above, another advantageous technique for producing the compositions according to the invention in a formulation with delayed release of active ingredient consists of embedding the active ingredients in suitable matrix substances from which the active ingredients are released in a delayed and controlled manner. The matrix which can be used for this purpose is, for example, the material employed for the enveloping. Production in this case is expediently carried out by dissolving or dispersing the active ingredients in the solution or dispersion of the enveloping material and subsequently applying this composition as described above for the enveloping substances to the carrier material. This ensures that the active ingredients are uniformly distributed in the enveloping layer. Release from these formulations is usually diffusion-controlled.

The fungicidal compositions generally contain, for example, from 0.01 to 95, preferably 0.05 to 90, % by weight of crop protection agent.

The application rates depend on the required effect and are from 0.02 to 5 kg, preferably 0.05 to 3 kg, crop protection agent per ha. The ratio of active ingredients in a binary fungicidal mixture is generally from 50:1 to 1:10, preferably 20:1 to 1:5, in particular 10:1 to 1:2.

The fungicidal compositions have excellent activity on a wide range of phytopathogenic fungi, in particular from the ascomycetes and basidiomycetes classes.

They are particularly important for controlling a large number of fungi on various crop plants such as cereals, eg. wheat, rye, barley, oats, rice, oilseed rape, sugar beet, corn, soybean, coffee, sugar cane, ornamentals and vegetables such as cucumbers, beans and cucurbits. The fungicides produced according to the invention are particularly advantageously used to control fungi on cereals.

The compositions are expediently applied by allowing the composition to act in or on the soil on the seeds which have been sown in the soil or on the plants which have developed therefrom, or on seedlings. The composition can be applied, and the seeds can be sown or the seedlings can be planted in separate steps, it being possible to apply the composition before or after the sowing of the seeds or the planting of the seedlings.

It is particularly advantageous to apply the formulated crop protection agents together with the seeds or the planting of the seedlings.

The preparation and use of the polymers according to the invention is explained in detail in the following Examples.

EXAMPLE 1

Production of a redispersible polyvinyl acetate: polyvinylpyrrolidone powder in the ratio 80:20 by weight and 5% by weight of polyvinyl alcohol.

500 g of vinyl acetate were emulsified in water with 0.5% by weight of sodium lauryl sulfate under nitrogen in a stirred vessel with reflux condenser and were polymerized by initiation with 0.3% by weight of sodium persulfate at 75° C. After addition of 5% by weight of polyvinyl alcohol (Mowiol® 8-88 from Hoechst), the reaction mixture was cooled to room temperature to result in a dispersion with a solids content of 27% by weight and an average particle size of 1 μm.

The dispersion was mixed with 417 g of a 30% by weight aqueous polyvinylpyrrolidone solution (Kollidon® K 30, from BASF) and the mixture was spray-dried in a cocurrent of nitrogen with an inlet temperature of 140° C. to result in a white, free-flowing powder.

EXAMPLE 2

Release-slowing coating on theophylline pellets

The release-slowing coating dispersion had the following composition:

| | |
|---|---|
| Titanium dioxide (from Kronos) | 0.5% by weight |
| Talc (from Riedel-de-Haen) | 4.0% by weight |
| Sicovit ® red 30 (from BASF) | 0.5% by weight |
| redispersible powder, consisting of polyvinyl acetate and polyvinylpyrrolidone in the ratio 80:20 by weight with 5.0% by weight of polyvinyl alcohol (Mowiol ® 8-88, from Hoechst) | 15.0% by weight |
| Water | 80.0% by weight |

The solids content was 20% by weight.

For production, first the redispersible powder was introduced into 70% of the amount of water with stirring and stirred for 15 minutes. A pigment suspension was prepared separately from titanium dioxide, talc and Sicovit® red 30 and 10% of the amount of water and was, after passing through a corundum disk mill, combined with the redispersed polymer dispersion. 671.0 g (including 10% overage for spray losses) of this coating dispersion were sprayed onto a fluidized bed of 500 g of theophylline pellets (Spherofillin 0.8 to 1.3 mm supplied by Knoll AG) in an Aeromatic Strea 1 (from Aeromatic).

The coating process was carried out under the following conditions:

| | |
|---|---|
| Nozzle | 0.8 mm |
| Preheating | 45° C./5 min |
| Inlet air rate | 100–130 m³/h |
| Inlet air temperature | 45° C. |
| Outlet air temperature | ca. 30° C. |
| Spraying mode | continuous |
| Spraying pressure | 0.8 bar |
| Spraying rate | 8.5 ml/min |
| Spraying time | ca. 80 min |
| Drying | 60° C./5 min |

A uniform smooth coating was produced.

To determine the release, the coated pellets, equivalent to an amount of 300 mg of theophylline, were packed in capsules and these were each introduced into 900 ml of simulated gastric fluid. Release was carried out in a paddle apparatus (from Pharmatest) at 37° C. and 50 rpm. After 2 hours, a phosphate buffer concentrate was added to buffer to pH 6.8.

The release results were as follows:

| | |
|---|---|
| 1 h | 14.5% |
| 2 h | 27.5% |
| 4 h | 37.4% |
| 8 h | 63.4% |
| 12 h | 79.4% |
| 16 h | 94.0% |
| 20 h | 100.0% |

The release was unchanged after storage at 30° C./70% rel. humidity and 40° C./75% rel. humidity for 6 months.

EXAMPLE 3

Release-slowing coating on caffeine pellets

The release-slowing coating dispersion had the following composition:

| | |
|---|---|
| redispersible powder consisting of polyvinyl acetate and polyvinylpyrrolidone in the ratio 80:20 by weight | 20.0% by weight |
| Talc | 5.0% by weight |
| Water | 75.0% by weight |

The solids content was 25% by weight. For production, talc was finely dispersed in the amount of water using an Ultra-turrax. The redispersible powder was then slowly introduced while stirring with a paddle stirrer and then stirred for a further 30 minutes.

700.0 g of this coating dispersion were sprayed onto a fluidized bed of 500 g of caffeine granules (0.5–1.0 mm) in an Aeromatic Strea 1 (from Aeromatic).

The coating process was carried out under the following conditions:

| | |
|---|---|
| Nozzle | 0.8 mm |
| Preheating | 45° C./5 min |
| Inlet air rate | 100–130 m³/h |
| Inlet air temperature | 50° C. |
| Outlet air temperature | ca. 30° C. |
| Spraying mode | continuous |
| Spraying pressure | 0.8 bar |
| Spraying rate | 10 ml/min |
| Spraying time | ca. 70 min |
| Drying | 60° C./5 min |

A uniform smooth coating was produced.

To determine the release, coated pellets, equivalent to an amount of 100 mg of caffeine, were packed in capsules and these were each introduced into 900 ml of simulated gastric fluid. Release was carried out in a paddle apparatus (from Pharmatest) at 37° C. and 50 rpm. After 2 hours, a phosphate buffer concentrate was added to buffer to pH 6.8.

The release results were as follows:

| | |
|---|---|
| 1 h | 8.3% |
| 2 h | 16.4% |
| 4 h | 40.6% |

| | |
|---|---|
| 8 h | 74.9% |
| 16 h | 97.2% |

The release was unchanged after storage at 30° C./70% rel. humidity and 40° C./75% rel. humidity for 6 months.

EXAMPLE 4

Instant release coating on propranolol tablets 5000 g of propranolol HCl tablets with the following composition

| | |
|---|---|
| Propranolol HCl | 40.0 mg |
| Ludipress ® (from BASF) | 195.0 mg |
| Kollidon ® VA 64 (from BASF) | 12.5 mg |
| Magnesium stearate | 2.5 mg |
| Total weight | 250.0 mg | with a weight of 250 mg and a diameter of 9 mm, biconvex form, were sprayed in an Accela-Cota 24" (from Manesty) with 1260 g (including 10% overage for spray losses) of a coating suspension of the following composition:

| | |
|---|---|
| redispersible powder consisting of polyvinyl acetate and polyvinylpyrrolidone in the ratio 50:50 by weight with 5% by weight of polyvinyl alcohol (Mowiol ® 8/88 from Hoechst) and 1% by weight of highly disperse silica | 10.0% by weight |
| Lutrol ® E 6000 (from BASF) | 1.0% by weight |
| Sicovit ® red 30 (from BASF) | 1.5% by weight |
| Titanium dioxide (from Kronos) | 3.0% by weight |
| Talc (from Riedel-de-Haen) | 4.5% by weight |
| Water | 80.0% by weight |

The coating suspension was produced in a similar way to that described in Example 2.

The solids content of the coating suspension was 20% by weight, and the amount applied was 6 mg of solid/cm² of tablet surface area. The tablet cores were coated under the following equipment conditions:

| | |
|---|---|
| Vessel | 12 rpm |
| Nozzle | 1.0 mm |
| Preheating | 60° C./5 min |
| Spraying pressure | 2.0 bar |
| Spraying mode | continuous |
| Differential pressure | −2 mm |
| Outlet air temperature | ca. 40° C. |
| Inlet air temperature | 60° C. |
| Spraying rate | 25 g/min |
| Drying | 60° C./5 min |

The film-coated tablets had a smooth uniform surface with not the slightest blurring of the imprint.

The film-coated tablets disintegrated in simulated gastric fluid in 7 minutes and thus complied with the requirements of the German Pharmacopeia for instant release forms (<15 minutes).

On release in simulated gastric fluid using the paddle apparatus at 37° C. and 50 rpm, more than 90% of the amount of medicinal substance was released after 30 minutes.

Release:

30 min 96.5%
60 min 99.5%

EXAMPLE 5

Instant release coating on propranolol tablets

The formula and processing were similar to Example 4 but with the use of redispersible powder consisting of polyvinyl acetate and polyvinylpyrrolidone in the ratio 70:30 by weight. 3% by weight of hydroxypropylmethylcellulose (Pharmacoat® 606 from Shin-etsu) was additionally added to the coating suspension.

Film-coated tablets had a smooth uniform surface with the imprint nicely formed. Disintegration took 6 minutes and the release after 30 minutes was 98.1%.

EXAMPLE 6

220 g of redispersible powder consisting of polyvinyl acetate and polyvinylpyrrolidone (Kollidon® 30, from BASF) in the ratio 10:1 by weight were redispersed in 860 g of water in a stirred vessel within 30 minutes. This coating dispersion was applied to carrier granules in a Hüttlin Kugel Coater (HKC 5). The carrier granules employed were 4000 g of fertilizer pellets with an average diameter of 1.25 mm. The carrier granules were preheated to 40° C. in the HKC 5 and then a mixture of 20% by weight fenpropimorph emulsion (36.7 g of active ingredient) and a 45% by weight epoxiconazole suspension (5.7 g of active ingredient) was sprayed onto the granules.

The polymer dispersion was applied as envelope to the carrier granules coated with the epoxiconazole and fenpropimorph active ingredients.

The coating process was carried out under the following conditions:

| | |
|---|---|
| 3 nozzles (three substance nozzles) | 0.8 mm |
| Weight of carrier granules | 4000 g |
| Air flow rate | 400 m³/h |
| Inlet air temperature | 50° C. |
| Product temperature | 40–42° C. |
| Outlet air temperature | 37.5–40° C. |
| Spraying mode | continuous |
| Spraying pressure | 1 bar |
| Spraying rate (for active ingredients and enveloping polymer) | 12 g/min |
| Process duration | 90 min |
| Subsequent drying time to a product temperature of 50° C. | 15 min |

A uniform smooth coating was produced.

The release rate of the active ingredients was determined in an elution apparatus. This was done by weighing 30 g of the carrier granules into a siphon vessel with sintered disk. 3750 g of water were pumped through the vessel in 24 h and collected. 124 mg of fenpropimorph and 18.5 mg of epoxiconazole were detected in the collected liquid.

EXAMPLE 7

130 g of redispersible powder consisting of polyvinyl acetate and polyvinylpyrrolidone (Kollidon® 30, from BASF) in the ratio 12:1 by weight were redispersed in 295 g of water in a stirred vessel within 45 min. This coating dispersion was applied to carrier granules in a Hüttlin Kugel Coater (HKC 5). The carrier granules employed were 3240 g of fertilizer pellets with an average diameter of 1.3 mm. The carrier granules were preheated to 40° C. in the HKC 5 and then a mixture of 20% by weight fenpropimorph emulsion (65.6 g of active ingredient) and a 45% by weight epoxiconazole suspension (21.9 g of active ingredient) was sprayed onto the granules.

The polymer dispersion was applied as envelope to the carrier granules coated with the epoxiconazole and fenpropimorph active ingredients.

The coating process was carried out under the following conditions:

| | |
|---|---|
| 3 nozzles (three substance nozzles) | 1.4 mm |
| Weight of carrier granules | 3240 g |
| Air flow rate | 280–300 m$^3$/h |
| Inlet air temperature | 60° C. |
| Product temperature | 43–45° C. |
| Outlet air temperature | 37.5–40° C. |
| Spraying mode | continuous |
| Spraying pressure | 0.8 bar |
| Spraying rate (for active ingredients and enveloping polymer) | 19 g/min |
| Process duration | 23 min |
| Subsequent drying time to a product ternperature of 50° C. | 15 min |

A uniform smooth coating was produced.

The release rate of the active ingredients was determined in an elution apparatus. This was done by weighing 30 g of the carrier granules into a siphon vessel with sintered disk. 3980 g of water were pumped through the vessel in 24 h and collected. 148 mg of fenpropimorph and 19 mg of epoxiconazole were detected in the collected liquid.

The coated product was applied with cereal seed (winter wheat) in October. On average, about 3 fungicidal agent pellets were deposited under the soil per seed grain. Epoxiconazole was detected in the growing cereal plants two months and six months after application. 0.038 mg/kg of green weight was detected two months after sowing, and there was still 0.022 mg/kg of green weight six months after application.

It was thus possible to show that controlled release of the active ingredient epoxiconazole can be ensured over at least 6 months in soil by the polyvinyl acetate/polyvinylpyrrolidone coating.

We claim:

1. A coating composition for pharmaceutical or agrochemical forms which consisting of a) 10–95% by weight of polyvinyl acetate, b) 5–90% by weight of an N-vinylpyrrolidone-containing polymer, c) 0–20% by weight of another water-soluble or water-swellable substance and d) 0–20% by weight of a water-insoluble dusting agent with or without e) other additives.

2. A composition as claimed in claim 1 which comprises as component b) a polymer from the group of polyvinylpyrrolidone, vinyl acetate/vinylpyrrolidone copolymers and mixtures thereof.

3. A composition as claimed in claim 1 which comprises as component c) a polymer from the group of cellulose derivatives, acrylate/methacrylate copolymers and polyvinyl alcohols or mixtures thereof.

4. A composition as claimed in claim 1 which comprises as component d) water-insoluble dusting agent from the group of cellulose, disperse silica, talc, bentonite, magnesium stearate and calcium phosphate or mixtures thereof.

5. A composition as claimed in claim 1 in the form of an aqueous dispersion.

6. A solid pharmaceutical or agrochemical composition having a core containing active ingredients and having a coating of a) 10–95% by weight of polyvinyl acetate, b) 5–90% by weight of an N-vinylpyrrolidone-containing polymer, c) 0–20% by weight of another water-soluble or water-swellable substance and d) 0–20% by weight of a water-insoluble dusting agent with or without e) other additives.

7. A solid pharmaceutical composition as claimed in claim 6, from which the active ingredients are released in a period of from 0.25 to 24 hours.

8. A solid agrochemical composition as claimed in claim 6, from which the active ingredients are released in a period of from 6 weeks to 6 months.

* * * * *

UNITED STATES PATENT AND TRADEMARK OFFICE
CERTIFICATE OF CORRECTION

PATENT : 6,046,277

DATED : April 4, 2000

INVENTOR(S) : KOLTER et al.

It is certified that error appears in the above-identified patent and that said Letters Patent is hereby corrected as shown below:

Column, 12, claim 6, line 30, after "coating" insert --consisting essentially--.

Signed and Sealed this

Fifteenth Day of May, 2001

Attest:

NICHOLAS P. GODICI

Attesting Officer    Acting Director of the United States Patent and Trademark Office